(12) United States Patent
Honda et al.

(10) Patent No.: US 9,122,067 B2
(45) Date of Patent: Sep. 1, 2015

(54) ENDOSCOPE

(71) Applicant: OLYMPUS CORPORATION, Tokyo (JP)

(72) Inventors: Kazuki Honda, Higashiyamato (JP); Yuichi Ikeda, Tama (JP); Sho Shinji, Fuchu (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 14/300,379

(22) Filed: Jun. 10, 2014

(65) Prior Publication Data

US 2014/0347878 A1    Nov. 27, 2014

Related U.S. Application Data

(63) Continuation of application No. PCT/JP2013/079378, filed on Oct. 30, 2013.

(30) Foreign Application Priority Data

Nov. 7, 2012   (JP) ................................ 2012-245668

(51) Int. Cl.
*A61B 1/07*    (2006.01)
*G02B 23/24*   (2006.01)
(Continued)

(52) U.S. Cl.
CPC ........ *G02B 23/2469* (2013.01); *A61B 1/00096* (2013.01); *A61B 1/051* (2013.01); *A61B 1/0607* (2013.01); *A61B 1/0615* (2013.01); *A61B 1/07* (2013.01); *G02B 23/243* (2013.01); *G02B 23/2461* (2013.01); *A61B 1/00177* (2013.01); *A61B 1/00181* (2013.01)

(58) Field of Classification Search
CPC ...... A61B 1/0607; A61B 1/0615; A61B 1/07; A61B 1/00177; A61B 1/00181; G02B 23/2469; G02B 6/262; G02B 5/09
See application file for complete search history.

(56) References Cited

U.S. PATENT DOCUMENTS 4,584,988 A  *  4/1986  Nishioka et al. .............. 600/177
4,671,630 A  *  6/1987  Takahashi ..................... 359/503
(Continued)

FOREIGN PATENT DOCUMENTS

EP         2476362 A1    7/2012
JP     2003-319903 A    11/2003
(Continued)

*Primary Examiner* — John P Leubecker
(74) *Attorney, Agent, or Firm* — Scully, Scott, Murphy & Presser, PC

(57) ABSTRACT

An endoscope according to the present invention includes: a first image pickup optical system for observing a first observation direction, a second image pickup optical system for observing an observation a second observation direction, a light guide guiding illumination light, and an illumination optical system including a ring-shaped portion illuminating the first observation direction, an incident surface being in contact with an end surface of the light guide to receive the illumination light, and two reflecting surfaces disposed at a position opposite to the incident surface, having inclinations in two directions with respect to a surface orthogonal to the longitudinal direction of the insertion portion, disposed so as to face each other, and reflecting the illumination light incident from the light guide toward directions along tangent lines of the ring-shaped portion of the illumination optical system, to cause the illumination light incident to inside of the illumination optical system.

14 Claims, 10 Drawing Sheets

(51) Int. Cl.
*A61B 1/06* (2006.01)
*A61B 1/05* (2006.01)
*A61B 1/00* (2006.01)

(56) References Cited

U.S. PATENT DOCUMENTS

| | | | | |
|---|---|---|---|---|
| 7,553,037 | B2* | 6/2009 | Sullivan | 362/26 |
| 7,712,907 | B2* | 5/2010 | Zyka | 362/16 |
| 2004/0066659 | A1* | 4/2004 | Mezei et al. | 362/555 |
| 2006/0139946 | A1* | 6/2006 | Tamaki | 362/602 |
| 2006/0256575 | A1* | 11/2006 | Vayser | 362/573 |
| 2009/0036744 | A1* | 2/2009 | Vayser | 600/182 |
| 2010/0312057 | A1* | 12/2010 | Konno | 600/162 |
| 2012/0157773 | A1* | 6/2012 | Honda et al. | 600/164 |
| 2013/0137923 | A1* | 5/2013 | Honda et al. | 600/109 |
| 2014/0286037 | A1* | 9/2014 | Matsuba | 362/553 |

FOREIGN PATENT DOCUMENTS

| | | |
|---|---|---|
| JP | 2010194191 A | 9/2010 |
| JP | 4955838 B2 | 6/2012 |
| WO | WO 2012/005049 A1 | 1/2010 |
| WO | WO 2012/137737 A1 | 10/2012 |

* cited by examiner

ENDOSCOPE

CROSS REFERENCE TO RELATED APPLICATION

This application is a continuation application of PCT/JP2013/079378 filed on Oct. 30, 2013 and claims benefit of Japanese Application No. 2012-245668 filed in Japan on Nov. 7, 2012, the entire contents of which are incorporated herein by this reference.

BACKGROUND OF THE INVENTION

1. Field of the Invention

The present invention relates to an endoscope capable of simultaneously observing a forward field of view and sideward field of view.

2. Description of the Related Art

In recent years, endoscopes have been widely used in the medical field and the industrial field. The endoscope enables observation of an inside of a subject with an elongated insertion portion inserted into the subject. A variety of types of such endoscopes have been proposed and put to practical use, such as a direct-viewing type endoscope in which an observation lens and an illumination lens are provided on a distal end surface of a distal end portion provided on a distal end side of an insertion portion, and a side-viewing type endoscope in which an observation lens and an illumination lens are provided on a part of a side surface of a distal end portion of an insertion portion.

Further, in recent years, various endoscopes have been proposed, in Japanese Patent No. 4955838, for example, and put to practical use, which are configured to be capable of simultaneously observing not only a forward field of view with respect to a distal end portion of an insertion portion, but also a field of view in a circumferential direction positioned sideward along a circumference of an outer circumferential side surface of a distal end portion in order to expand the observation range.

This type of endoscope is configured to be provided with, for example, a forward-observing objective lens that forms an image of the forward field of view and a sideward-observing objective lens which is provided behind the forward-observing objective lens and forms an image of the sideward field of view to allow a wide field of view to be observed. In this case, some sideward-observing objective lenses are configured to serve also as forward-observing objective lenses.

This configuration enables simultaneous observation of a sideward field of view in a circumferential direction in addition to a forward field of view with respect to a distal end portion of an insertion portion of an endoscope.

Japanese Patent Application Laid-Open Publication No. 2003-319903 and Japanese Patent Application Laid-Open Publication No. 2010-194191, for example, disclose illuminating means for the conventional types of endoscopes, configured to provide a ring-shaped optical system member so as to surround a circumferential edge of a forward-observing lens placed on a distal end surface of an insertion portion and cause a light flux from a light guide fiber to be incident to the ring-shaped optical system member.

SUMMARY OF THE INVENTION

An endoscope according to one aspect of the present invention includes: a first image pickup optical system that is disposed in an insertion portion to be inserted into a lumen and for observing an observation object in a first observation direction; a second image pickup optical system that is disposed in the insertion portion and for observing an observation object in a second observation direction which is different from the first observation direction; a light guide that guides illumination light emitted from a light source to the insertion portion; an illumination optical system that is disposed in the insertion portion and includes a ring-shaped portion for illuminating the first observation direction; an incident surface that is provided to the illumination optical system, is in contact with an end surface of the light guide to receive the illumination light, and formed orthogonal to a longitudinal direction of the insertion portion; and two reflecting surfaces that are disposed at a position opposite to the incident surface, the two reflecting surfaces having inclinations in two directions with respect to a surface orthogonal to the longitudinal direction of the insertion portion, disposed so as to face each other, the two reflecting surfaces reflecting the illumination light incident from the light guide to the incident surface toward directions along tangent lines of the ring-shaped portion of the illumination optical system, to cause the illumination light incident to inside of a ring-shaped optical portion.

DETAILED DESCRIPTION OF THE PREFERRED EMBODIMENT(S)

Figure 1:
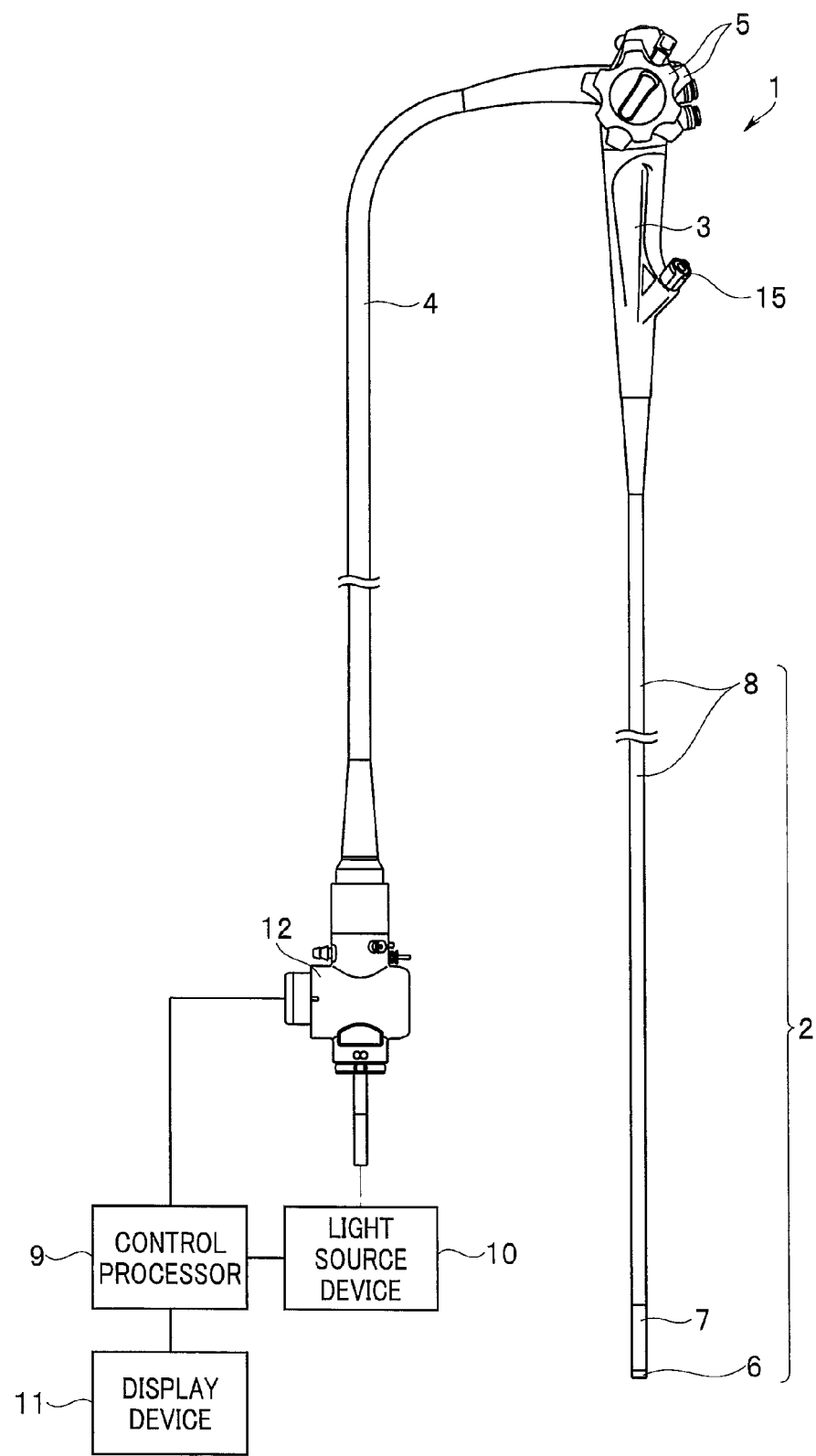
FIG. 1 is a schematic configuration view showing an entire configuration of an endoscope according to one embodiment of the present invention.

Hereinafter, the present invention will be described with embodiments shown in drawings. Note that different drawings for the following descriptions may contain portions of elements having different ratios of dimensions in order to allow the each element to be illustrated in a recognizable size in the drawings. Therefore, quantity of the elements, shapes of the elements, ratios of dimensions of the elements, and relations of relative positions of respective elements are not limited to those in the embodiments shown in the drawings.

Figure 2:
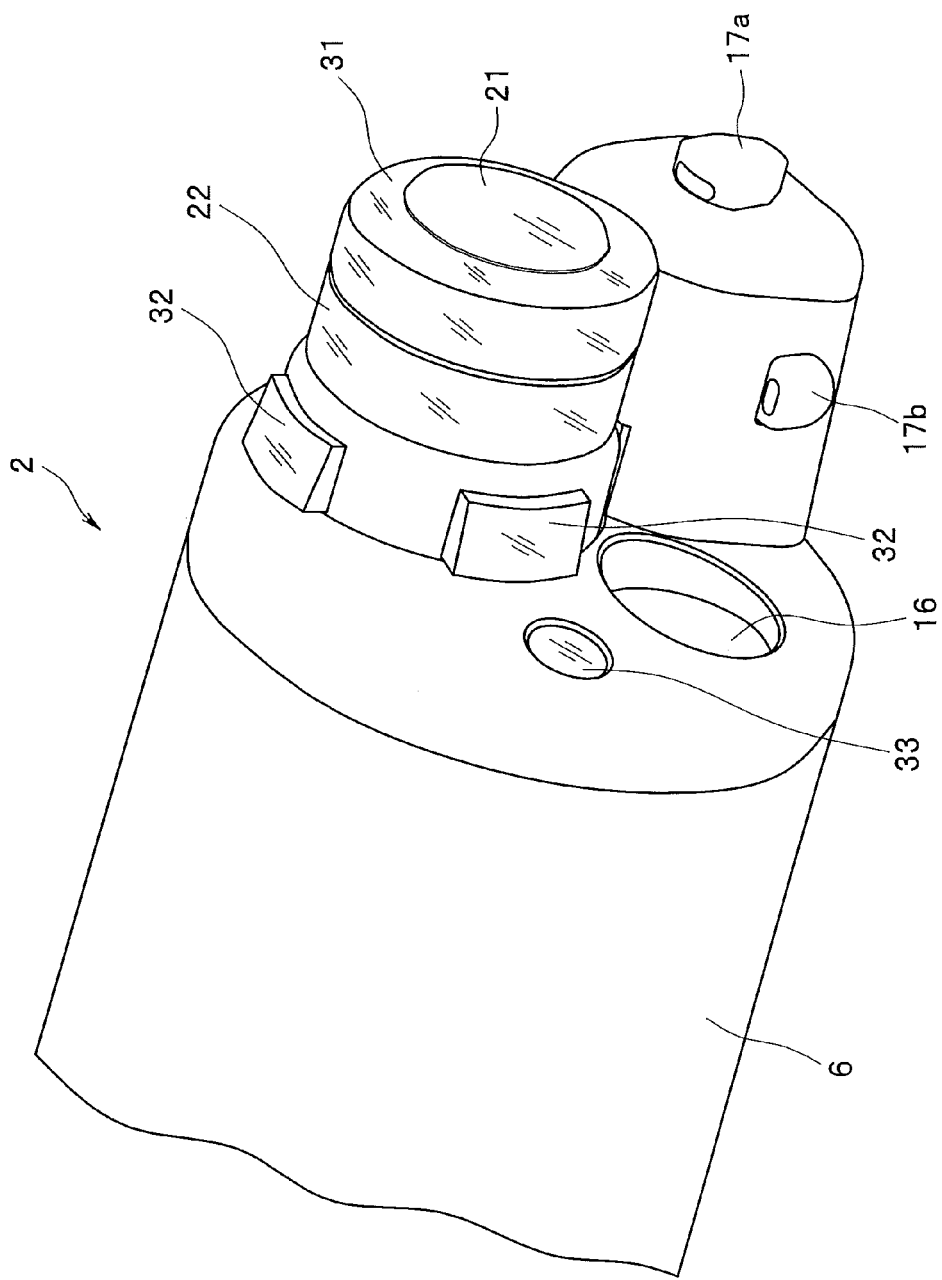
FIG. 2 is an enlarged main part perspective view enlargedly showing a distal end portion of an insertion portion of the endoscope in FIG. 1.
Figure 3:
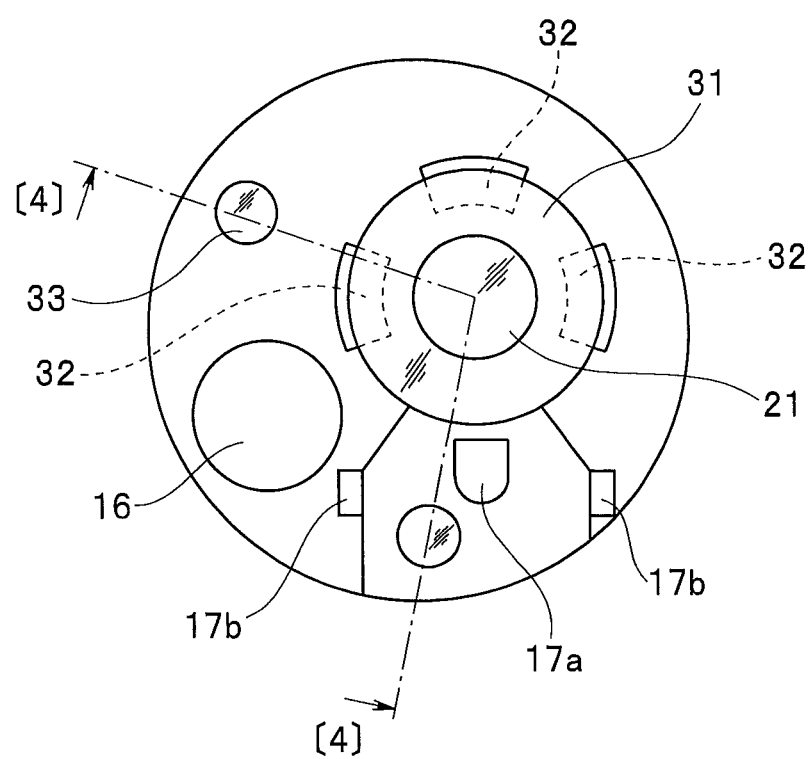
FIG. 3 is a front view of the distal end portion of the insertion portion in FIG. 2.
Figure 4:
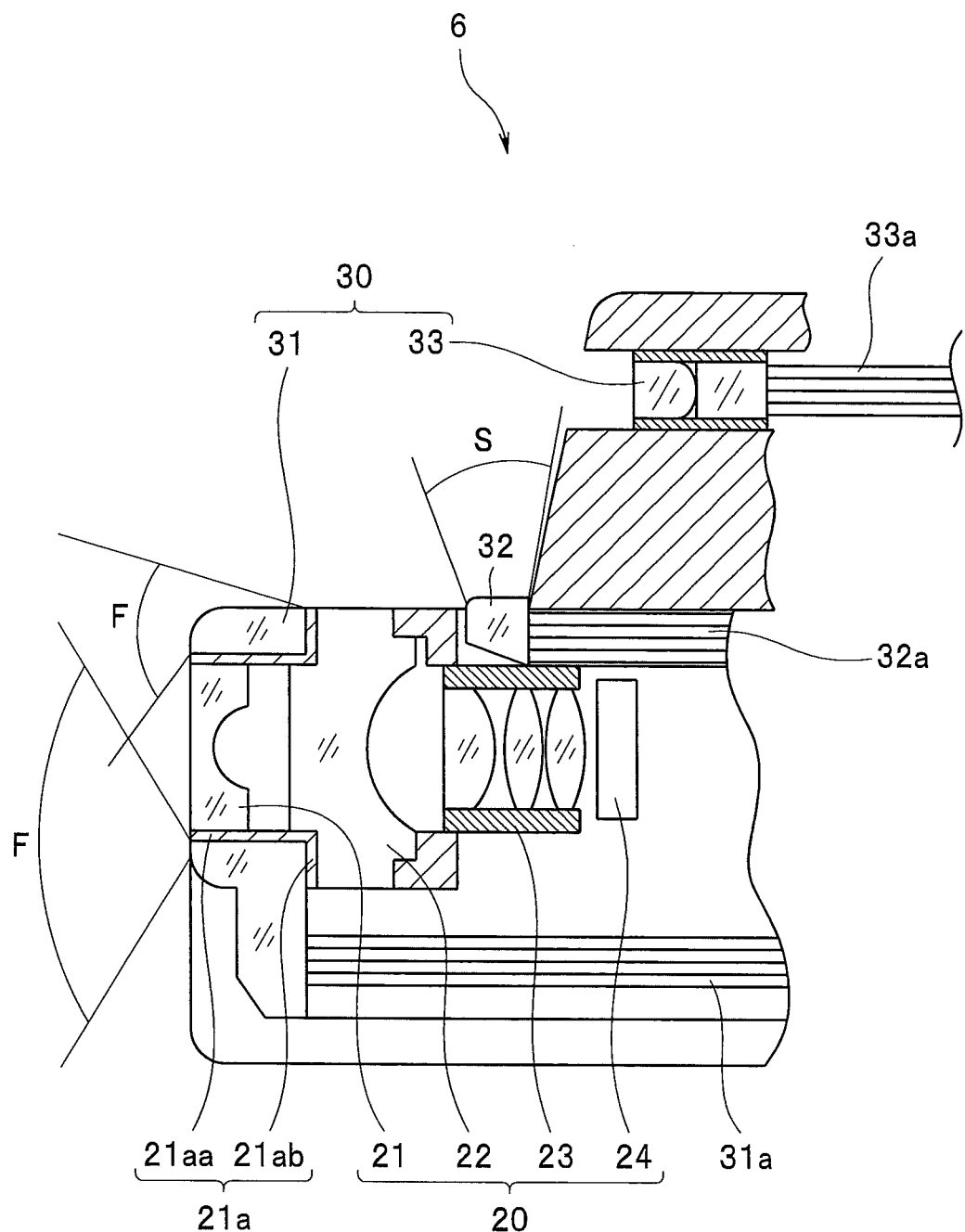
FIG. 4 is a sectional view taken along the line [4]-[4] in FIG. 3.
Figure 5:
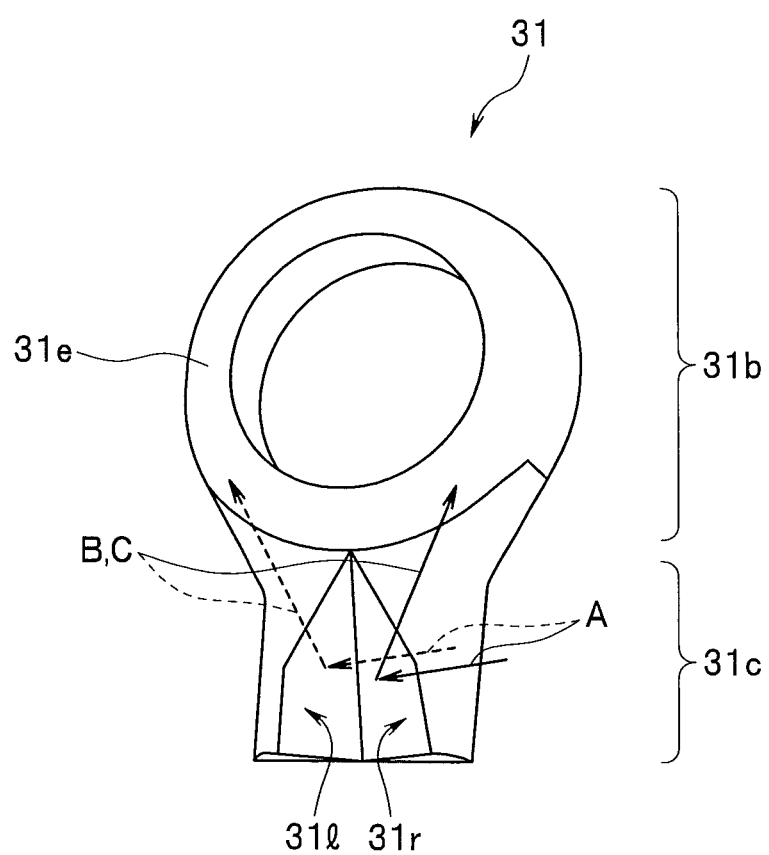
FIG. 5 is a perspective view of a light-guiding body included in an illumination unit of the endoscope in FIG. 1 as seen from a front side.
Figure 6:
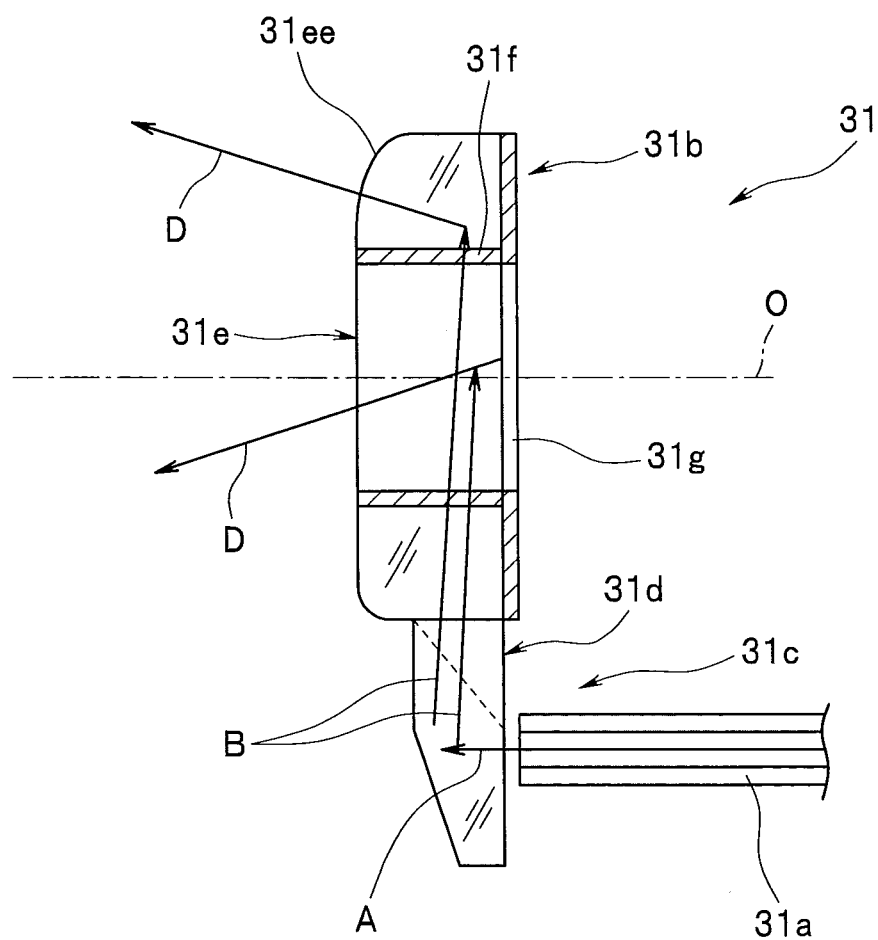
FIG. 6 is a side view of the light-guiding body included in the illumination unit of the endoscope in FIG. 1.
Figure 7:
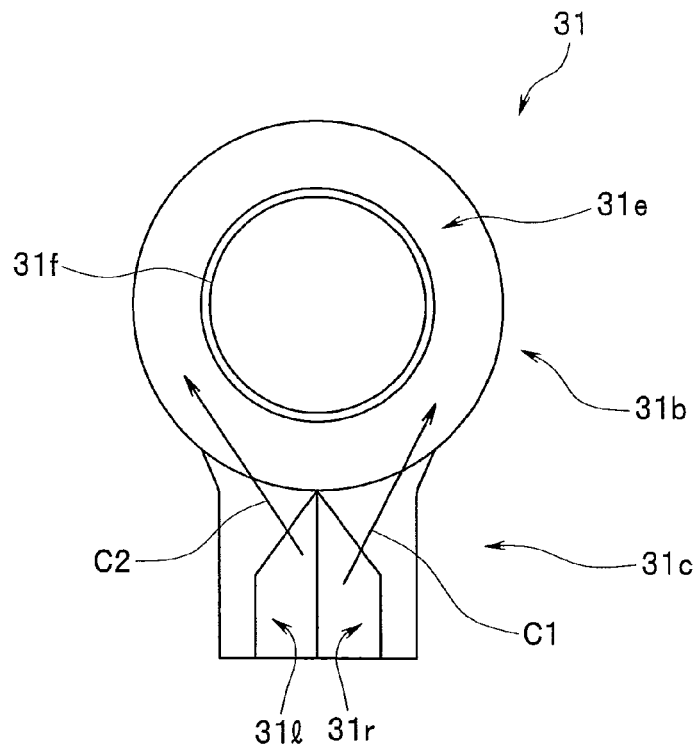
FIG. 7 is a front view of the light-guiding body included in the illumination unit of the endoscope in FIG. 1.

First, the schematic configuration of an endoscope according to one embodiment of the present invention will be briefly described below. FIG. 1 is a schematic configuration view showing an entire configuration of an endoscope according to one embodiment of the present invention. FIG. 2 is an enlarged main part perspective view enlargedly showing a distal end portion of an insertion portion of the endoscope in FIG. 1. FIG. 3 is a front view of the distal end portion of the insertion portion in FIG. 2. FIG. 4 is a sectional view taken along the line [4]-[4] in FIG. 3. FIGS. 5 to 7 are views showing only a light-guiding body included in an illumination unit in the endoscope in FIG. 1. FIG. 5 is a perspective view of the light-guiding body as seen from a front side. FIG. 6 is a side view of the light-guiding body. FIG. 7 is a front view of the light-guiding body.

As shown in FIG. 1, the endoscope 1 mainly includes an elongated insertion portion 2 to be inserted into a body cavity or the like, an operation portion 3 connected on a proximal end side of the insertion portion 2, a universal code 4 extended from the operation portion 3, a connector portion 12 provided at an end portion of a universal code 4, and the like.

Note that the endoscope 1 according to the present embodiment is a wide-field-of-view-type endoscope which allows simultaneous observation of a forward field of view and a sideward field of view, wherein a forward-observing objective lens 21 and forward-illuminating lenses 31, 33 are provided on a distal end surface of a distal end portion 6 of the insertion portion 2, oriented forward for direct viewing, and a sideward-observing objective lens 22 and a sideward-illuminating lens 32 are provided close to the forward-observing objective lens 21, as shown in FIGS. 2 to 4, etc.

Here, the forward-observing objective lens 21 is a first objective lens that forms an image of an observation object in a forward direction of the insertion portion 2 and is disposed on the distal end side of the insertion portion 2 to be inserted into a lumen. Further, the sideward-observing objective lens 22 is a second objective lens having a circumferential shape that forms an image of an observation object in a sideward direction of the insertion portion 2 and is disposed on a proximal end side of the insertion portion 2 with respect to the forward-observing objective lens 21 (first objective lens).

Returning to FIG. 1, the insertion portion 2 is constituted of the rigid distal end portion 6 provided on the distal-most end portion, a bending portion 7 connected to the proximal end side of the distal end portion 6, and a flexible tube portion 8 connected on a proximal end side of the bending portion 7 and made of a flexible and elongated tubular member.

Inside the distal end portion 6 of the insertion portion 2 are placed an image pickup unit 20 and an illumination unit 30, for example, as shown in FIG. 4. On the distal end surface of the distal end portion 6 are placed a treatment instrument channel opening 16, the forward-observing objective lens 21, illuminating lenses 31, 32 and 33, and water feeding nozzles 17a, 17b, for example, as shown in FIGS. 2 and 3.

Inside the insertion portion 2 are inserted, for example, a treatment instrument channel (not shown), a plurality of light guides (31a, 32a, 33a; see FIG. 4), a signal cable (not shown), and the like. The treatment instrument channel is inserted from the treatment instrument channel opening 16 at the distal end surface, to pass through the insertion portion 2, and communicates with a treatment instrument insertion port 15 of the operation portion 3. Further, the plurality of light guides and the signal cable are extended from respective configuration units in the distal end portion 6 of the insertion portion 2, inserted through the insertion portion 2, inserted through inside the universal code 4 via inside the operation portion 3, and finally communicate with the connector portion 12 at the end of the universal code 4. Note that each of the plurality of light guides (31a, 32a, 33a) is a fiber bundle formed by bundling many light guide fibers to transmit an illumination light. That is, the plurality of light guides (31a, 32a, 33a) are guiding means for guiding the illumination light emitted from a light source to the distal end side of the insertion portion 2 (to be detailed later).

An endoscope system including the endoscope 1 according to the present embodiment is configured by connecting the endoscope 1 with a control processor 9, a light source device 10, a display device 11, and the like that are external devices via the connector portion 12.

The operation portion 3 is a site to be grasped by a user when using the endoscope 1, and on the outer surface of the operation portion 3 are placed a bending operation knob 5 and a plurality of operation members that correspond to various other actions. The bending operation knob 5, for example, is an operation member that allows the bending portion 7 of the insertion portion 2 to bend in any of up, down, right and left directions through a rotating operation with the user's fingers or the like.

The treatment instrument insertion port 15 from which a treatment instrument (not shown) or the like is to be inserted is formed on a site close to a distal end of the operation portion 3 and in the vicinity of a connection site with the insertion portion 2. The treatment instrument insertion port 15 communicates with the treatment instrument channel (not shown) passing through the insertion portion 2.

The light source device 10 is a device that generates illumination light. The control processor 9 is a signal processing device for generally controlling the entire endoscope system. The display device 11 is a display portion for displaying an endoscope image on the basis of image pickup signals obtained by the endoscope 1. An LCD panel, for example, is applied to the display device 11.

The control processor 9, the light source device 10, and the display device 11 are connected with the endoscope 1 via the connector portion 12. The control processor 9 thus transmits control signals, various detection signals, and obtained image signals via the signal cable inserted through inside the endoscope 1. Then, the control processor 9 transmits processed image signals to the display device 11 and causes the display device 11 to display the endoscope image, various information, etc. Also, the light source device 10 is connected with the plurality of light guides (31a, 32a, 33a) inserted through inside the endoscope 1. With such a configuration, the illumination light from the light source device 10 is guided via the connector portion 12 to the universal code 4, the operation portion 3, and the plurality of light guides (31a, 32a, 33a) in the insertion portion 2, then, guided to the illumination unit 30 provided in the distal end portion 6 of the insertion portion 2, and emitted outward through each of the illuminating lenses 31, 32 and 33 on the distal end surface.

The illumination unit 30 is constituted of the plurality of illuminating lenses (31, 32, 33), the plurality of light guides (31a, 32a, 33a), etc. The illuminating lens 31 of the plurality of illuminating lenses (31, 32, 33) serves as a forward-illuminating optical system, the forward-illuminating lens, and the forward-illuminating light-guiding body, for emitting the illumination light to illuminate a direction opposing to the distal end surface of the endoscope 1, that is, a forward direction. The illuminating lens 32 serves as a sideward-illuminating optical system, the sideward-illuminating lens, and a sideward-illuminating light-guiding body, for emitting the illumination light to illuminate a direction orthogonal to the distal end surface of the endoscope 1, that is, a sideward direction. The illuminating lens 33 serves as an auxiliary forward-illuminating optical system for emitting an auxiliary illumination light to supplementary illuminate the forward direction of the endoscope 1. The illuminating lenses 31, 32 and 33 are respectively connected with the ends of the corresponding plurality of light guides (31a, 32a, 33a) and are configured to allow the illumination light guided from the light source device 10 to be incident to the lenses, as described above. Note that the light guide 31a of the plurality of light guides is a first light guide for forward-illuminating, the light guide 32a is a second light guide for sideward-illuminating, and the light guide 33a is a third light guide for auxiliary forward-illuminating.

Note that the sideward-illuminating lens 32 is configured by including a prism or the like that changes the direction of the illumination light guided from the second light guide 32a and causes the illumination light to be emitted in a sideward direction of the insertion portion 2, while at the same time causing a part of the illumination light to be emitted in the forward direction of the insertion portion 2.

The forward-illuminating lens of the plurality of illuminating lenses (hereinafter referred to as "forward-illuminating lens") 31 is formed of a transparent member having a ring shape, and serves as a light-guiding body that is formed by integrating a ring portion 31b that diffuses the incident light and emits the diffused light in one direction, and a light polarization portion 31c made of a transparent member, that is connected with the first light guide 31a and receives the illumination light emitted from the first light guide 31a and guides the light to the ring portion 31b.

More specifically, the ring portion 31b is disposed so as to surround the outer circumference of the forward-observing objective lens 21 (first objective lens), is disposed in a site facing a front surface on the outer circumference side of the sideward-observing objective lens 22 (second objective lens), and is a ring-shaped optical portion having a ring shape. The ring portion 31b has an optical directivity to be described later.

Further, the light polarization portion 31c is a light-guiding portion that causes the illumination light guided to the distal end side of the insertion portion 2 by the first light guide 31a to be incident to the ring portion 31b (ring-shaped optical portion). To this end, the light polarization portion 31c is formed to have a light incident surface 31d that is in contact with an emission end surface of the first light guide 31a and to which the illumination light of the first light guide 31a (see arrow A in FIG. 6) is incident, and two light-reflecting surfaces 31r, 31l that are formed on a site facing the light incident surface 31d and reflect the incident illumination light from the light incident surface 31d (arrow A) upward as seen from a side surface shown in FIG. 6 (see arrow B in FIG. 6) and obliquely upward as seen from a front surface shown in FIG. 7 (see arrows C1, C2 in FIG. 7).

In other words, the light incident surface 31d of the light polarization portion 31c is formed in parallel with a surface orthogonal to a longitudinal direction of the insertion portion 2, is in contact with the end surface of the first light guide 31a, and serves as an incident surface to which the illumination light guided by the first light guide 31a is incident.

Further, the two light-reflecting surfaces 31r, 31l of the light polarization portion 31c are disposed in a position facing the light incident surface 31d, have inclinations in two directions with respect to the face orthogonal to the longitudinal direction of the insertion portion 2, disposed so as to face each other, and serve as reflecting surfaces to reflect the illumination light incident from the first light guide 31a to the light incident surface 31d. Each of the two light-reflecting surfaces 31r, 31l reflects the illumination light in a direction along a tangent line of the ring portion 31b (ring-shaped optical portion) and causes the illumination light to be incident to inside the ring portion 31b.

In this case, since the first light guide 31a is inserted through the insertion portion 2 of the endoscope 1 as described above, the first light guide 31a is placed along the longitudinal direction, that is, axial direction of the endoscope 1. More specifically, the first light guide 31a is provided in parallel with the longitudinal direction of the insertion portion 2 at a site adjacent to the outer circumference of the sideward-observing objective lens 22 (second objective lens).

The illumination light emitted from the emission end surface of the first light guide 31a is also emitted in the same direction as the longitudinal direction, that is, the axial direction of the endoscope 1. Positioning of the forward-illuminating lens 31 is made such that the light incident surface 31d of the light polarization portion 31c of the forward-illuminating lens 31 is disposed to be orthogonal to the longitudinal direction or the axial direction of the endoscope 1, that is, to the emission end surface of the first light guide 31a.

Moreover, the light-reflecting surfaces 31r, 31l are formed in a valley shape that makes an inward convex as seen from the front shown in FIGS. 5 and 7. In FIG. 7, out of the incident light from the light incident surface 31d, the incident light to light-reflecting surface 31r that is a right half portion as seen from the front is reflected obliquely right upward as seen from the front, as shown by the arrow C1. On the other hand in FIG. 7, out of the incident light from the light incident surface 31d, the incident light to the light-reflecting surface 31l that is a left half portion as seen from the front is reflected obliquely left upward as seen from the front, as shown by the arrow C2. The illumination light reflected by each of the light-reflecting surfaces 31r, 31l is thus guided toward the ring portion 31b, as shown in FIGS. 5 to 7. Then, as shown by the arrow D in FIG. 6, the illumination light is diffused in the ring portion 31b and finally emitted from a light emission surface 31e on the front surface side toward the forward direction.

To this effect, the ring portion 31b of the forward-illuminating lens 31 is provided with a reflective member 31f that is formed on a ring-shaped inner circumferential surface of the ring portion 31b, having a function of reflecting the illumination light, which is incident to the inside of the ring portion 31b and on the inner circumferential surface, toward the inside of the ring portion 31b, and serving as an optical processing portion formed of a thin-film-shaped member having a high reflectivity for illumination light, (for example, an aluminum material). The reflective member 31f also functions as a surface that reflects the illumination light incident inward from the light emission surface 31e side toward the inside of the ring portion. In other words, the reflective member 31f is provided on the inner circumference of the ring portion 31b, and the reflective member 31f serves as the optical processing portion that reflects the illumination light, which is guided by the first light guide 31a and incident to the ring portion 31b, toward the inside of the ring portion 31b.

Note that, instead of the above embodiment in which the reflective member 31f is provided on the entire circumference of the inner circumferential surface of the ring portion 31b having the ring shape, the reflective member 31f may be placed at least in a site on the incident side of the illumination light, that is, a site facing the light polarization portion 31c, on the inner circumferential surface having the ring shape.

Furthermore, on a ring-shaped surface of a back side (surface on the proximal end side of the insertion portion 2) opposing the light emission surface 31e on the front surface side of the ring portion 31b, a light diffusing surface 31g serving as a diffusing portion for diffusing the illumination light inside the ring portion 31b, and reflecting and emitting the diffused illumination light in a forward direction of the ring portion 31b. The light diffusing surface 31g is formed such that, for example, the ring surface is subjected to a satin finish processing to form projections and recesses on the ring surface, and the processed surface is further applied with a coating material such as a reflective paint having a high light reflexivity. In another embodiment, a processing for forming projections and recesses on a surface is applied according to a modification example to be described later (see FIGS. 9 and 10).

The light emission surface 31e of the ring portion 31b is processed such that a cross section of the outer circumferential edge portion on the front surface side provides a curved surface portion 31ee, as shown in FIG. 6. Such a shape allows the illumination light emitted from inside the ring portion 31b through the curved surface portion 31ee to refract so as to get closer to a direction along the center axis of the ring portion 31b (the axis coincident with an optical axis of an image pickup optical system: reference sign O in FIG. 6) in the curved surface portion 31ee, and the illumination light is thus emitted forward.

Such a configuration enables substantially even illumination of the observation range of the forward-observing objective lens 21 in the direction in which the distal end surface of the insertion portion 2 faces opposing the distal end surface of the insertion portion 2, that is, the forward direction of the insertion portion 2 in the body cavity into which the insertion portion 2 is inserted. Note that a reference sign F in FIG. 4 schematically represents the range to be illuminated by the illumination light emitted from the forward-illuminating lens 31. A reference sign S schematically represents the range to be illuminated by the illumination light emitted from the sideward-illuminating lens 32.

The cross-sectional shape of the outer circumferential edge portion on the front surface side of the light emission surface 31e of the ring portion 31b may be, for example, an inclined surface oriented forward and toward the optical axis O side, instead of a curved surface shape of the curved surface portion 31ee, as described above.

On the other hand, the forward-observing objective lens 21 of the image pickup unit 20 is disposed in the ring-shaped inner part of the ring portion 31b of the forward-illuminating lens 31. The image pickup unit 20 includes the forward-observing objective lens (hereinafter referred to as "forward-observing lens") 21, the sideward-observing objective lens 22, a rear-group optical system 23 constituted of a plurality of optical lenses and a lens-holding frame, and an image pickup device 24 that is a photoelectric conversion element such as a charge coupled device, as shown in FIG. 4. With this configuration, an observation image of the forward field of view is formed in a predetermined region on a light receiving surface of the image pickup device 24 via the forward-observing lens 21 and the rear-group optical system 23. At the same time, an observation image of the sideward field of view is formed in a predetermined region on the light receiving surface of the image pickup device 24 via the sideward-observing objective lens 22 and the rear-group optical system 23. Responding to this, the image pickup device 24 performs a predetermined photoelectric conversion processing, and the thus-obtained image pickup signals are inputted to the control processor 9 via the signal cable. The control processor 9 performs various types of signal processings on the inputted image pickup signals and outputs the generated image signals to the display device 11. In response to this, the display device 11 displays the corresponding endoscope image.

As described above, the forward-observing lens 21 of the image pickup unit 20 is disposed on the ring-shaped inner part of the ring portion 31b of the forward-illuminating lens 31. In this case, the forward-observing lens 21 and the sideward-observing objective lens 22 are fixed and held with respect to the distal end portion 6 by an objective lens barrel 21a formed with a light-shielding member. The ring-shaped inner part of the ring portion 31b of the forward-illuminating lens 31 is disposed so as to be fitted into the outer circumference of a cylinder-shaped portion 21aa of the objective lens barrel 21a. In this state, a back surface side of an outer circumferential edge portion of the ring portion 31b is disposed so as to face the front surface side of the outer circumferential edge portion of the sideward-observing objective lens 22 with a flange portion 21ab of the objective lens barrel 21a sandwiched therebetween. This provides a configuration to prevent the illumination light emitted from the forward-illuminating lens 31 from being incident to the forward-observing lens 21 and the sideward-observing objective lens 22.

The endoscope 1 with such a configuration according to the present embodiment is used in a state of being connected with the light source device 10 via the connector portion 12 of the universal code 4. In this state, turning on the power of the light source device 10 to emit the illumination light causes the illumination light to be guided toward the distal end side of the insertion portion 2 by the plurality of light guides (31a, 32a, 33a). Then, the illumination light is emitted from the end surfaces on the distal end sides of the plurality of light guides (31a, 32a, 33a).

The end surface on the distal end side of first light guide 31a of the plurality of light guides is in contact with the light incident surface 31d of the forward-illuminating lens 31. This causes the illumination light emitted from the end surface on the distal end side of the first light guide 31a to be incident perpendicularly to the light incident surface 31d. After that, the illumination light is reflected by the light-reflecting surfaces 31r, 31l. The reflected light is mainly guided toward inside the ring portion 31b. Then, the illumination light guided to inside the ring portion 31b is reflected and diffused by the reflective member 31f, the light diffusing surface 31g, and other elements inside the ring portion 31b, and is finally efficiently emitted forward from the front surface side of the light emission surface 31e, as shown in an arrow D in FIG. 6.

Note that the forward-illuminating lens serving as the light-guiding body applied to the illumination unit in the endoscope according to the above embodiment is not limited to the above embodiment, but may be a different embodiment to be described below.

Figure 8:
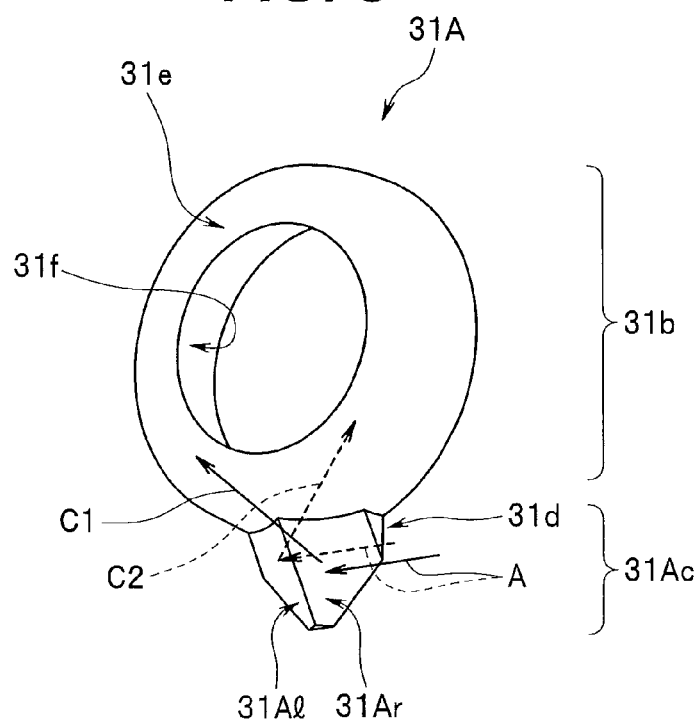
FIG. 8 shows a modification example of a light-guiding body (forward-illuminating lens) applied to an endoscope of the present invention.

FIG. 8 is a view showing a modification example of the light-guiding body (forward-illuminating lens) applied to the endoscope according to the one embodiment of the present invention. A forward-illuminating lens 31A according to the modification example in FIG. 8 serves as the light-guiding body formed by integrating the ring portion 31b and a light polarization portion 31Ac. The configuration of the ring portion 31b is totally the same as that of the ring portion 31b of the forward-illuminating lens 31 according to the above-described one embodiment.

On the other hand, the light polarization portion 31Ac of the forward-illuminating lens 31 according to the present embodiment is formed to include the light incident surface 31*d* which is in contact with the emission end surface of the first light guide 31*a* and to which the illumination light of the first light guide 31*a* (see the arrow A in FIG. 8) is incident and light-reflecting surfaces 31Ar, 31Al that are formed in a site opposing the light incident surface 31*d* and reflect the illumination light incident from the light incident surface 31*d* (the arrow A) upward as seen from a side surface (not shown) and obliquely upward (see the arrows C1, C2 in FIG. 8) as seen from a front surface (not shown).

Here, the light-reflecting surfaces 31Ar, 31Al are formed in a ridge shape that makes a convex toward a front direction as seen from the front surface, as shown in FIG. 8. In FIG. 8, out of the incident light from the light incident surface 31*d*, the incident light to the light-reflecting surface 31Ar that is a right-half portion as seen from the front is reflected obliquely left upward as seen from the front, as shown by the arrow C1. On the other hand, in the FIG. 8, out of the incident light from the incident surface 31*d*, the incident light to the light-reflecting surface 31Al that is a left-half portion as seen from the front is reflected obliquely right upward as seen from the front, as shown by the arrow C2. As described above, the illumination light reflected by each of the light-reflecting surfaces 31Ar, 31Al is guided toward the ring portion 31*b*, is diffused in the ring portion 31*b*, and is finally emitted forward from the light emission surface 31*e* of the front surface side. Note that the configuration of the ring portion 31*b* in the forward-illuminating lens 31A is the same as that of the above embodiment.

Employment of the forward-illuminating lens 31A thus configured yields the same effect as that of the above embodiment.

Figure 9:
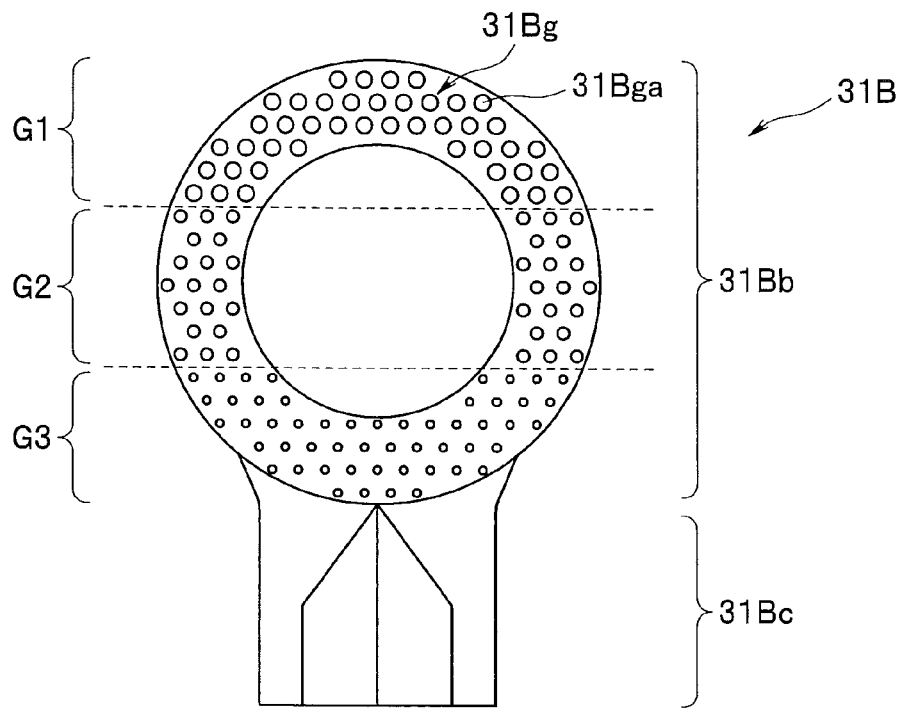
FIG. 9 shows another modification example of a light-guiding body (forward-illuminating lens) applied to an endoscope of the present invention, and is a view showing a back side (light diffusing surface) of the light-guiding body (forward-illuminating lens).
Figure 10:
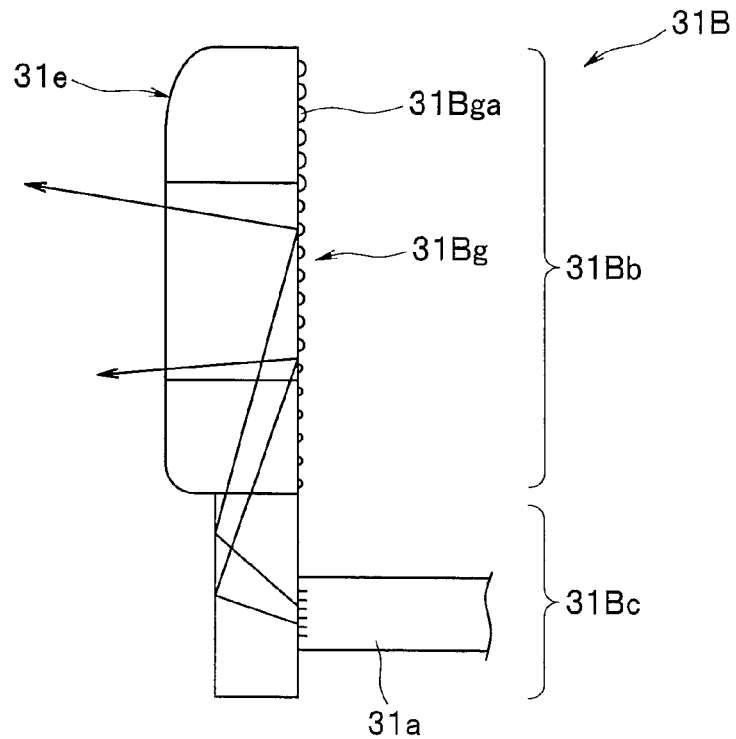
FIG. 10 is a side view of the light-guiding body (forward-illuminating lens) in FIG. 9.

Further, FIGS. 9 and 10 are views showing another modification example of the light-guiding body (forward-illuminating lens) applied to the endoscope according to the one embodiment of the present invention. FIG. 9 is a view showing a back surface side (light diffusing surface) of the light-guiding body (forward-illuminating lens) according to the present modification example. FIG. 10 is a side view of the light-guiding body (forward-illuminating lens) according to the present modification example.

The basic configuration of the forward-illuminating lens 31B shown in the present modification example is substantially the same as that of the forward-illuminating lens 31 of the endoscope according to the above-mentioned embodiment except only for the surface shape of a light diffusing surface 31Bg.

In the present modification example, a ring surface on a back side of a ring portion 31Bb of the forward-illuminating lens 31B, that is, the light diffusing surface 31Bg is subjected to a surface treatment by which a plurality of substantially hemispheric-shaped projection-and-recess portions (hereinafter referred to as "hemispheric projection-recess portions") 31Bga protruded outward from the ring surface are disposed, as shown in FIGS. 9 and 10. Surfaces of the hemispheric projection-recess portions 31Bga are configured to be covered with mirror coating or a light reflective coating portion, for example.

In this case, the hemispheric projection-recess portions 31Bga serving as a diffusing portion are formed so as to change the diffusibility such that the farther the hemispheric projection-recess portions 31Bga are from the first light guide 31*a*, the greater the diffusion effect of the illumination light becomes.

Specifically, as shown in FIG. 9, for example, a plurality of sizes (three types for the present example) of the hemispheric projection-recess portions 31Bga are prepared and disposed on a predetermined region for each size. Here, for example, when the light diffusing surface 31Bg is seen from a position opposing the light diffusing surface 31Bg of the ring portion 31Bb, three regions G1, G2 and G3 that are triple-divided the light diffusing surface 31Bg in the horizontal direction are described below. Sizes of hemispheric projection-recess portions 31Bga disposed on the respective regions G1, G2 and G3 are configured to be different. In this case, the size of hemispheres of the hemispheric projection-recess portions 31Bga is large in a region represented with the reference sign G1, which is distant from the light polarization portion 31Bc (that is, the incident position of the illumination light), the size of hemispheres of the hemispheric projection-recess portions 31Bga is middle in a region represented with the reference sign G2, which is middle of the light diffusing surface 31Bg, and the size of hemispheres of the hemispheric projection-recess portions 31Bga is small in a region represented with the reference sign G3, which is close to the light polarization portion 31Bc. Other configurations are substantially the same as that of the above embodiment.

Applying the forward-illuminating lens 31B serving as the light-guiding body thus configured in the above other modification example also yields the same effect as that of the above-mentioned embodiment.

With this configuration, since the size of the hemispheres of the hemispheric projection-recess portions 31Bga becomes larger as the region becomes farther from the light polarization portion 31Bc (incident position of the illumination light), even if the light quantity decreases because of being far from the incident position, a great light diffusion effect can be obtained by the hemispheric projection-recess portions 31Bga having the large-sized hemispheres. Thus, the luminance unevenness on the light emission surface 31*e* due to the distance from the incident position of illumination light can be reduced and the light can be evenly emitted from the emission surface 31*e*.

Note that the example mentioned above shows the embodiment in which the sizes of the hemispheric projection-recess portions 31Bga are limited to three types. However, the present invention is not limited to the embodiment, but the light diffusing surface 31Bg may be formed to have hemispheres whose sizes become larger as being farther from the incident position of the light polarization portion 31Bc (incident position of illumination light), for example.

On the other hand, the endoscope 1 according to the present embodiment is provided with the sideward-observing objective lens 22 and the sideward-illuminating lens 32 on the outer circumferential surface of the distal end portion 6 as described above, thereby allowing simultaneous observation of the sideward field of view and the forward field of view. Here, the detailed configuration of the illuminating lens according to the present endoscope 1 will be described with reference to FIGS. 2, 3, 4, 11, and 12.

Figure 11:
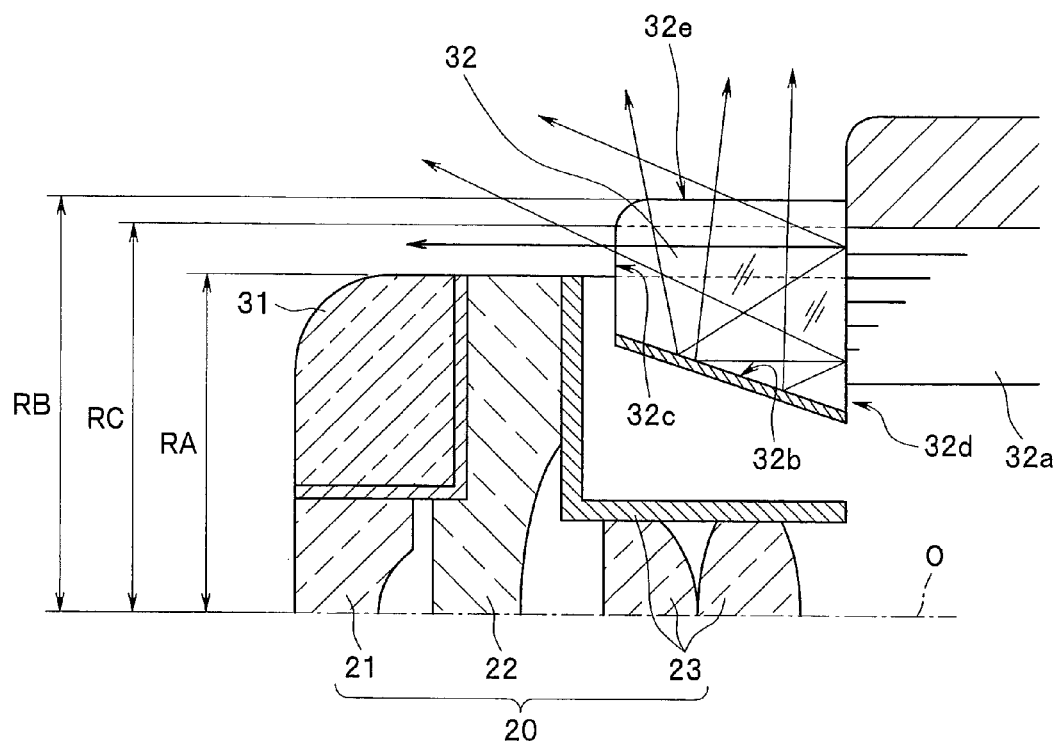
FIG. 11 is an enlarged main part sectional view enlargedly showing a part of the distal end portion of the insertion portion of the endoscope according to the one embodiment of the present invention.
Figure 12:
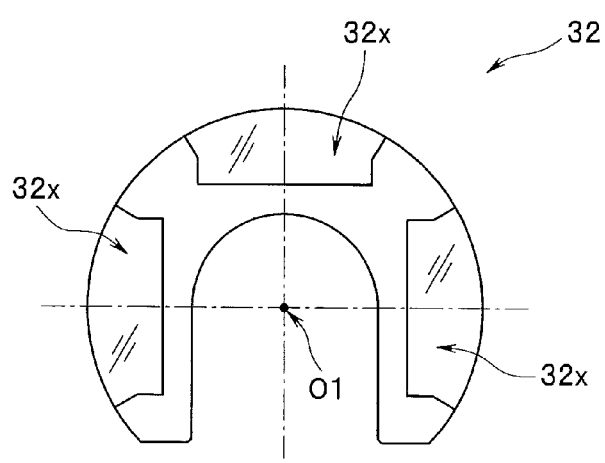
FIG. 12 is a schematic front view showing only a sideward-illuminating lens to be applied to the endoscope in FIG. 1.

FIG. 11 is an enlarged main part sectional view enlargedly showing a part of the distal end portion of the insertion portion of the endoscope according to the one embodiment of the present invention. Note that FIG. 11 is a view enlargedly showing a part of FIG. 4, but omitting the details in order to prevent complexity of the drawing. Therefore, shapes of respective elements are shown a little differently, but the components assigned with the same reference signs are regarded as the same members. In FIG. 11, the reference sign O represents an optical axis of the image pickup optical system (21, 22, 23) of the image pickup unit 20. FIG. 11 shows an upper half of the optical axis O. FIG. 12 is a schematic front view showing only the sideward-illuminating lens to be applied to the endoscope according to the present embodiment.

As described above, in the endoscope 1 according to the present embodiment the forward-observing lens 21 of the image pickup unit 20 is disposed at the ring-shaped inner part of ring portion 31b of the forward-illuminating lens 31. The sideward-observing objective lens 22 is provided behind the forward-observing lens 21 along the optical axis O, and the rear-group optical system 23 is placed further behind. The sideward-illuminating lens 32 is placed on the outer circumferential surface of the rear-group optical system 23. The entirety of the sideward-illuminating lens 32 is formed in a horseshoe shape as seen from front, as shown in FIG. 12. The center point (the reference sign O1 in FIG. 12) of an arc shape of the sideward-illuminating lens 32 is placed so as to align with the optical axis O of the image pickup optical system (21, 22, 23) of the image pickup unit 20. Thus, the center point O1 of the sideward-illuminating lens 32 and the optical axis O of the image pickup optical system (21, 22, 23) are aligned with each other to secure an even light distribution in the sideward direction. Note that the entirety of the sideward-illuminating lens 32 may be formed with a transparent member, for example, and may be configured to include light-guiding portions formed with transparent members in a plurality of regions (reference sign 32x) along the outer circumference, as shown in FIG. 12.

The sideward-illuminating lens 32 is formed with a substantially transparent member and configured to have light-guiding portions 32x each constituted of a polyhedron including at least a light incident surface 32d, a forward emission surface 32c, a sideward emission surface 32e, and a light scattering surface 32b.

The light incident surface 32d is provided on the surface facing backward in the sideward-illuminating lens 32. The light incident surface 32d is in contact with the emission end surface of the second light guide 32a. Here, the second light guide 32a is provided on a proximal end side of the sideward-illuminating lens 32 (second objective lens) in parallel with the longitudinal direction of the insertion portion 2 and guides the illumination light emitted from the light source device 10 to the distal end side of the insertion portion 2. Then, the illumination light emitted from each of the light incident surfaces of the second light guide 32a is caused to be incident to the inside of the sideward-illuminating lens 32 by passing through each of the light incident surfaces 32d. According to a cross section in FIG. 11, the light scattering surface 32b having inclination toward the light incident surface 32d is formed on the bottom side between the light incident surface 32d and the opposing face (forward emission surface 32c). The inner surface of each of the light scattering surfaces 32b is subjected to a surface treatment which allows the illumination light incident from the light incident surface 32d to be reflected and scattered toward the inside of the sideward-illuminating lens 32. As the surface treatment for the light scattering surface 32b, for example, substantially the same surface treatment as that for the light diffusing surface 31g of the forward-illuminating lens 31 is applied.

The sideward-illuminating lens 32 is formed with the forward emission surfaces 32c facing the forward direction of the endoscope 1 and the sideward emission surfaces 32e facing the sideward direction of the endoscope 1, and configured such that most of the illumination light from the second light guide 32a passes through the sideward emission surfaces 32e and is emitted in the sideward direction of the endoscope 1, and at the same time, some of the illumination light is emitted forward from the forward emission surfaces 32c.

Thus, in the cross section in FIG. 11, the disposition of the sideward-illuminating lens 32 is set so as to satisfy the relation of RB>RC>RA; where RA represents a distance from the optical axis O of the image pickup optical system (specifically, forward-observing lens 21) to the outermost circumferential surface of the sideward-observing objective lens 22; where RB represents a distance from the optical axis O of the image pickup optical system (specifically, forward-observing lens 21) to the outermost circumferential surface (sideward emission surface 32e) of the sideward-illuminating lens 32; and where RC represents a distance from the optical axis O of the image pickup optical system (specifically, forward-observing lens 21) to the outside outer circumferential surface of the second light guide 32a.

With this setting, a part of the sideward-illuminating lens 32 (forward emission surfaces 32c) and a part of the second light guide 32a are disposed on the further outer circumference side with respect to the outermost circumferential surface of the sideward-observing objective lens 22 in a radial direction of the distal end portion of the insertion portion of the endoscope 1. With this configuration, most of the illumination light from the second light guide 32a is scattered by the light scattering surfaces 32b inside the sideward-illuminating lens 32, and is emitted from the sideward emission surfaces 32e to the sideward direction of the endoscope 1, and at the same time, some of the illumination light passes through the sideward-illuminating lens 32 and is emitted forward from the forward emission surfaces 32c. Thus, compared with the light distribution to the sideward field of view of (a subject such as a wall surface in a relatively close position from) the endoscope 1, the light quantity of the light distribution to the forward field of view (subject inside a lumen in a relatively far position) of the endoscope 1 can be increased. Therefore, the entire field of view can be evenly illuminated.

Figure 13:
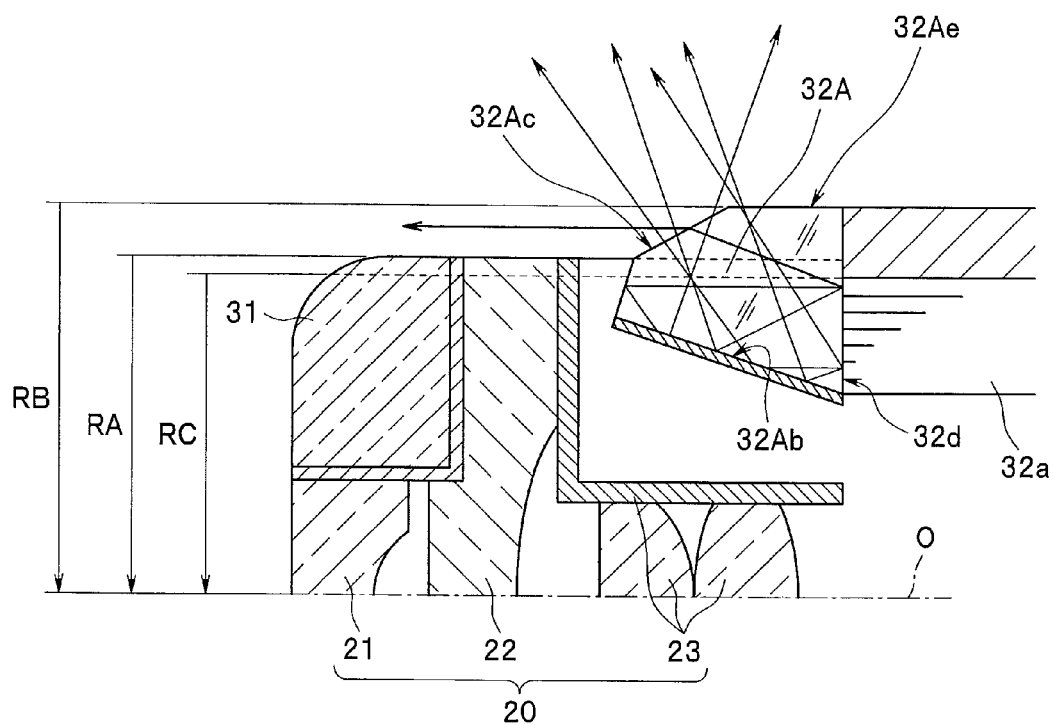
FIG. 13 is an enlarged main part sectional view showing a modification example of the endoscope according to the one embodiment of the present invention and enlargedly showing a part of the distal end portion of the insertion portion.

The configuration of the sideward-illuminating lens that can be applied to the present embodiment is not limited to the above-mentioned example, but may be a modification example shown in FIG. 13, for example. FIG. 13 is a view showing the modification example of the endoscope according to the one embodiment of the present invention and an enlarged main part sectional view enlargedly showing a part of the distal end portion of the insertion portion. The configuration of the endoscope according to the modification example is substantially the same as that of the endoscope according to the above-mentioned embodiment and only differs in the sideward-illuminating lens. Therefore, description for the same configuration as that of the above-mentioned embodiment is omitted, and only the different configuration will be described below.

Also, at the distal end portion of the insertion portion of the endoscope in the modification example, a sideward-illuminating lens 32A is placed on the outer circumferential surface of the rear-group optical system 23.

The sideward-illuminating lens 32A in the modification example is formed with a substantially transparent member in the same manner as the sideward-illuminating lens 32 according to the above-mentioned embodiment and has light-guiding portions each constituted of a polyhedron including at least a light incident surface 32d, a forward emission surface 32Ac, a sideward emission surface 32Ae, and a light scattering surface 32Ab.

Each of the light incident surfaces 32d is provided on the surface oriented backward in the sideward-illuminating lens 32A. The light incident surfaces 32d are in contact with the emission end surfaces of the second light guide 32a. The illumination light of the second light guide 32a passes through each of the light incident surfaces 32d and is incident to the inside of the sideward-illuminating lens 32A. In the cross section in FIG. 13, on a bottom surface side of the sideward-illuminating lens 32A is formed a light scattering surface 32Ab inclined toward the light incident surface 32*d* side. The inner surface of each of the light scattering surfaces 32Ab is subjected to a surface treatment so as to reflect and scatter the illumination light incident from each of the light incident surfaces 32*d* toward the inside of the sideward-illuminating lens 32A. The surface treatment for the light scattering surfaces 32Ab is substantially the same as the surface treatment applied to the light scattering surfaces 32*b* of the sideward-illuminating lens 32 in the above-mentioned embodiment.

The sideward-illuminating lens 32A includes the forward emission surface 32Ac inclined in the forward direction of the endoscope 1 and the sideward emission surface 32Ae connected consecutively with the forward emission surface 32Ac, extended on the proximal end side and oriented in the sideward direction of the endoscope 1. Most of illumination light from the second light guide 32*a* passes through the sideward emission surface 32Ae and is emitted in the sideward direction of the endoscope 1. At the same time, some of the illumination light is emitted forward by refracting on the forward emission surface 32*c*.

To this end, the disposition of the sideward-illuminating lens 32A in the cross section in FIG. 13 is set to satisfy the relation of RB>RA>RC; where RA represents the distance from the optical axis O of the image pickup optical system (specifically, forward-observing lens 21) to the outermost circumferential surface of the sideward-observing objective lens 22; where RB represents the distance from the optical axis O of the image pickup optical system (specifically, forward-observing lens 21) to the outermost circumferential surfaces (sideward emission surface 32Ae) of the sideward-illuminating lens 32A; and where RC represents the distance from the optical axis O of the image pickup optical system (specifically, forward-observing lens 21) to the outside outer circumferential surface of the second light guide 32*a*.

With this setting, only a part of the sideward-illuminating lens 32A (each of the forward emission surfaces 32Ac) is disposed on the outer circumference side with respect to the outermost circumferential surface of the sideward-observing objective lens 22 in the radial direction of the distal end portion of the insertion portion of the endoscope 1. With this configuration, the same effects as those of the above-mentioned embodiment can be obtained. Further, in the configuration of the modification example, the protrusion amount of the sideward-illuminating lens 32A in the radial direction of the distal end portion of insertion portion can be restricted.

According to the first embodiment as described above, the devised configuration of the light polarization portion 31*c* of the forward-illuminating lens 31 allows the illumination light emitted from the first light guide 31*a* disposed in the longitudinal direction or the axial direction of the endoscope 1 in the same direction to be efficiently guided to the ring portion 31*b* provided in a direction orthogonal to the longitudinal direction or the axial direction of the endoscope 1.

The forward-illuminating lens 31 includes the ring portion 31*b* that is formed in a ring shape so as to surround the outer circumference side of the forward-observing lens 21. Thus, the ring portion 31*b* allows the illumination light guided from the first light guide 31*a* to be substantially evenly emited from the light emission surface 31*e* of the ring portion 31*b* in the forward direction, that is, the observation range (image pickup range) of the forward-observing lens 21.

At the same time, some of the illumination light emitted from the second light guide 32*a* for sideward illumination is emitted forward by the devised disposition and shape of the sideward-illuminating lens 32. It is thus enabled to increase the light quantity of the light distribution for forward illumination and secure more even light distribution between the forward field of view and the sideward field of view.

Note that the present invention is not limited to the embodiments described above, and various changes or modifications can be made within the range not departing from the gist of the present invention. Further, the embodiments includes inventions of various stages, and various inventions can be extracted by appropriately combining the plurality of disclosed configuration requirements. For example, when a problem to be solved by the invention can be solved and effects of the invention are obtained even after some of the configuration requirements are omitted from the entire configuration requirements shown in the embodiment, then the configuration eliminating the configuration requirements can be extracted as an invention.

The present invention can be applied not only to a control device for an endoscope in the medical field, but also to a control device for an endoscope in the industrial field.

What is claimed is:

1. An endoscope comprising:
   a first image pickup optical system that is disposed in an insertion portion to be inserted into a lumen and for observing an observation object in a first observation direction;
   a second image pickup optical system that is disposed in the insertion portion and for observing an observation object in a second observation direction which is different from the first observation direction;
   a light guide that guides illumination light emitted from a light source to the insertion portion;
   an illumination optical system that is disposed in the insertion portion and includes a ring-shaped portion for illuminating the first observation direction;
   an incident surface that is provided to the illumination optical system, is in contact with an end surface of the light guide to receive the illumination light, and formed orthogonal to a longitudinal direction of the insertion portion; and
   two reflecting surfaces that are disposed at a position opposite to the incident surface, the two reflecting surfaces having inclinations in two directions with respect to a surface orthogonal to the longitudinal direction of the insertion portion, disposed so as to face each other, the two reflecting surfaces reflecting the illumination light incident from the light guide to the incident surface toward directions along tangent lines of the ring-shaped portion of the illumination optical system, to cause the illumination light incident to inside of the illumination optical system.

2. The endoscope according to claim 1, wherein the illumination optical system includes an optical processing portion that reflects the illumination light guided from the light guide toward inside of the illumination optical system, the optical processing portion being provided in a position including an inner circumferential surface of the illumination optical system.

3. The endoscope according to claim 2, wherein the optical processing portion is provided in a site other than a region from which the illumination light that is guided from the light guide and incident to the illumination optical system is emitted in the longitudinal direction of the insertion portion.

4. The endoscope according to claim 1, wherein the illumination optical system includes a light-guiding portion that causes the illumination light guided by the light guide to be incident to the ring-shaped portion.

5. The endoscope according to claim 1, wherein the illumination optical system is disposed to surround an outer circumference side of the first image pickup optical system.

6. The endoscope according to claim 1, further comprising:
a second light guide that guides the illumination light emitted from the light source to the insertion portion; and
a second illumination optical system including a prism that changes an orientation of the illumination light guided from the second light guide and causes the illumination light to be emitted toward the second observation direction, the prism at the same time causing a part of the illumination light to be emitted toward the first observation direction.

7. The endoscope according to claim 6, wherein
the first image pickup optical system, the second image pickup optical system, and the second illumination optical system are substantially coaxially provided, and are formed to each include a circle-shaped outer circumferential portion, and
the second image pickup optical system, the second illumination optical system, and the second light guide are disposed so as to satisfy a relation of RB>RC>RA, where
RA represents a distance from an optical axis of the first image pickup optical system to an outermost circumferential surface of the second image pickup optical system;
RB represents a distance from the optical axis of the first image pickup optical system to an outermost surface of the second illumination optical system; and
RC represents a distance from the optical axis of the first image pickup optical system to an outside outer circumferential surface of the second light guide.

8. The endoscope according to claim 6, wherein
the first image pickup optical system, the second image pickup optical system, and the second illumination optical system are substantially coaxially provided, and are formed to each include a circle-shaped outer circumferential portion, and
the second image pickup optical system, the second illumination optical system, and second light guide are disposed so as to satisfy a relation of RB>RA>RC, where
RA represents a distance from an optical axis of the first image pickup optical system to an outermost circumferential surface of the second image pickup optical system;
RB represents a distance from an optical axis of the first image pickup optical system to an outermost surface of the second illumination optical system; and
RC represents a distance from an optical axis of the first image pickup optical system to an outside outer circumferential surface of the second light guide.

9. The endoscope according to claim 6, wherein the light guide is provided so as to be adjacent to an outer circumference of the second image pickup optical system and parallel with the longitudinal direction of the insertion portion.

10. The endoscope according to claim 1, wherein
the first observation direction is a forward observation direction of the insertion portion, and the second observation direction is a sideward observation direction of the insertion portion, and
the first image pickup optical system is disposed on a distal end side of the insertion portion and forms an image of an observation object in a forward direction of the insertion portion, and the second image pickup optical system forms an image of an observation object in a sideward direction of the insertion portion.

11. The endoscope according to claim 1, wherein
the first image pickup optical system includes a first objective lens, and the second image pickup optical system includes a second objective lens, and
the second objective lens is disposed on a proximal end side of the insertion portion with respect to the first objective lens.

12. The endoscope according to claim 1, wherein the illumination optical system includes a diffusing portion provided on a surface on the proximal end side of the insertion portion, the diffusing portion scattering the illumination light and causes the scattered illumination light to be emitted forward the insertion portion.

13. The endoscope according to claim 12, wherein the diffusing portion is formed to have varying diffusibility such that the farther from the light guide, the greater a diffusing effect of the illumination light becomes.

14. The endoscope according to claim 1, wherein an inclined surface or a smooth curved surface oriented forward and toward an optical axis side is formed on a front surface side of an outer circumferential edge portion of the ring-shaped portion in the illumination optical system.

* * * * *